US012678100B2

(12) United States Patent
Wyckoff et al.

(10) Patent No.: US 12,678,100 B2
(45) Date of Patent: Jul. 14, 2026

(54) PATIENT MONITORING PATCH

(71) Applicant: THE BOEING COMPANY, Chicago, IL (US)

(72) Inventors: Nicholas Martin Wyckoff, Huntsville, AL (US); John D. Williams, Decatur, AL (US); Michael Francis Mitchell, Madison, AL (US)

(73) Assignee: THE BOEING COMPANY, Arlington, VA (US)

( * ) Notice: Subject to any disclaimer, the term of this patent is extended or adjusted under 35 U.S.C. 154(b) by 991 days.

(21) Appl. No.: 17/371,283

(22) Filed: Jul. 9, 2021

(65) Prior Publication Data

US 2023/0008262 A1 Jan. 12, 2023

(51) Int. Cl.
*G16H 10/60* (2018.01)
*A61B 5/00* (2006.01)
(Continued)

(52) U.S. Cl.
CPC .......... *A61B 5/6832* (2013.01); *A61B 5/0002* (2013.01); *A61B 5/01* (2013.01); *A61B 5/02438* (2013.01); *A61B 5/0245* (2013.01); *A61B 5/1112* (2013.01); *A61B 5/282* (2021.01); *A61B 5/339* (2021.01); *A61B 5/6801* (2013.01);
(Continued)

(58) Field of Classification Search
CPC ....... A61B 5/6832; A61B 5/0002; A61B 5/01; A61B 5/02438; A61B 5/0245; A61B 5/1112; A61B 5/282; A61B 5/339; A61B 5/6801; A61B 5/6833; A61B 5/024;
(Continued)

(56) References Cited

U.S. PATENT DOCUMENTS 7,434,730 B2    10/2008  Jain
7,548,802 B2     6/2009  Avery et al.
(Continued)

FOREIGN PATENT DOCUMENTS

JP        2011048734 A        3/2011

OTHER PUBLICATIONS

Extended European Search Report for Application No. 22168544.9 dated Oct. 10, 2022, pp. 1-6.
(Continued)

*Primary Examiner* — Joanne M Rodden
*Assistant Examiner* — Dana Stumpfoll
(74) *Attorney, Agent, or Firm* — Moore IP Law

(57) ABSTRACT

A device for monitoring a patient includes a substrate, an adhesive layer coupled to a first side of the substrate, and a circuit board coupled to a second side of the substrate. The adhesive layer is configured to adhere to a patient. The device also includes a plurality of switches coupled to the circuit board. Each switch is associated with a respective condition and is switchable by a user between a first state indicating that a corresponding condition is believed to be associated with the patient and a second state indicating that the corresponding condition is not believed to be associated with the patient. The device also includes a wireless transmitter coupled to the circuit board. The wireless transmitter is configured to transmit medical information associated with the patient to a mobile device. The medical information includes data indicating a setting of each of the plurality of switches.

20 Claims, 7 Drawing Sheets

(51) Int. Cl.

| | |
|---|---|
| *A61B 5/01* | (2006.01) |
| *A61B 5/024* | (2006.01) |
| *A61B 5/0245* | (2006.01) |
| *A61B 5/11* | (2006.01) |
| *A61B 5/282* | (2021.01) |
| *A61B 5/339* | (2021.01) |
| *G16H 40/20* | (2018.01) |
| *G16H 40/67* | (2018.01) |
| *H04W 12/033* | (2021.01) |

(52) U.S. Cl.

CPC .......... *A61B 5/6833* (2013.01); *G16H 10/60* (2018.01); *G16H 40/20* (2018.01); *G16H 40/67* (2018.01); *H04W 12/033* (2021.01); *A61B 5/024* (2013.01); *A61B 5/7475* (2013.01); *A61B 2562/0209* (2013.01)

(58) Field of Classification Search

CPC .......... A61B 2562/0209; G16H 10/60; G16H 40/20; G16H 40/67; H04W 12/033

See application file for complete search history.

(56) References Cited

U.S. PATENT DOCUMENTS

| | | | |
|---|---|---|---|
| 7,689,329 B2 | 3/2010 | Avery et al. | |
| 7,761,201 B2 | 7/2010 | Avery et al. | |
| 8,036,955 B2 | 10/2011 | Avery et al. | |
| 8,423,430 B2 | 4/2013 | Avery et al. | |
| 9,852,599 B1 * | 12/2017 | Slavin ...................... | A61B 7/04 |
| 10,079,829 B2 | 9/2018 | Angus | |
| 10,552,802 B2 | 2/2020 | Avery et al. | |
| 10,832,579 B2 * | 11/2020 | Patel ...................... | G16H 40/20 |
| 2003/0038047 A1 * | 2/2003 | Sleva ...................... | A61B 50/31 206/370 |
| 2012/0215075 A1 * | 8/2012 | Surace ................. | A61B 5/0002 600/301 |
| 2014/0121473 A1 * | 5/2014 | Banet ................... | A61B 5/6808 600/301 |
| 2015/0031321 A1 | 1/2015 | Nakamori et al. | |
| 2016/0296159 A1 * | 10/2016 | Larson ................... | G16H 20/00 |
| 2017/0020399 A1 * | 1/2017 | Shemesh .............. | A61B 5/0245 |
| 2017/0340221 A1 * | 11/2017 | Cronin .............. | A61B 5/02438 |
| 2018/0214161 A1 * | 8/2018 | Carabajal ............ | A61B 5/0036 |
| 2019/0174208 A1 * | 6/2019 | Speicher ................ | G06F 1/163 |
| 2020/0029134 A1 * | 1/2020 | Hoffmann ................ | H04Q 9/00 |
| 2020/0381094 A1 | 12/2020 | Myers et al. | |

OTHER PUBLICATIONS

"Chip-type Ceramic Rechargeable Batter "EnerCera" Series", NIK Insulators, https://www.ngk-insulators.com/en/product/enercera. html, retrieved May 4, 2021, 7 pgs.

Communication pursuant to Article 94(3) EPC for application No. 22168544.9 dated Nov. 20, 2024, pp. 1-3.

\* cited by examiner

200

MOBILE DEVICE
300

290

MEDICAL INFORMATION 210

FIRST CONDITION STATUS 208A

SECOND CONDITION STATUS 208B

THIRD CONDITION STATUS 208C

FOURTH CONDITION STATUS 208D

FIFTH CONDITION STATUS 208E

PATIENT MONITORING PATCH IDENTIFICATION NUMBER 220

HEART-RATE INFORMATION 124

TIMESTAMP 152

TEMPERATURE DATA 222

DATA 224

100

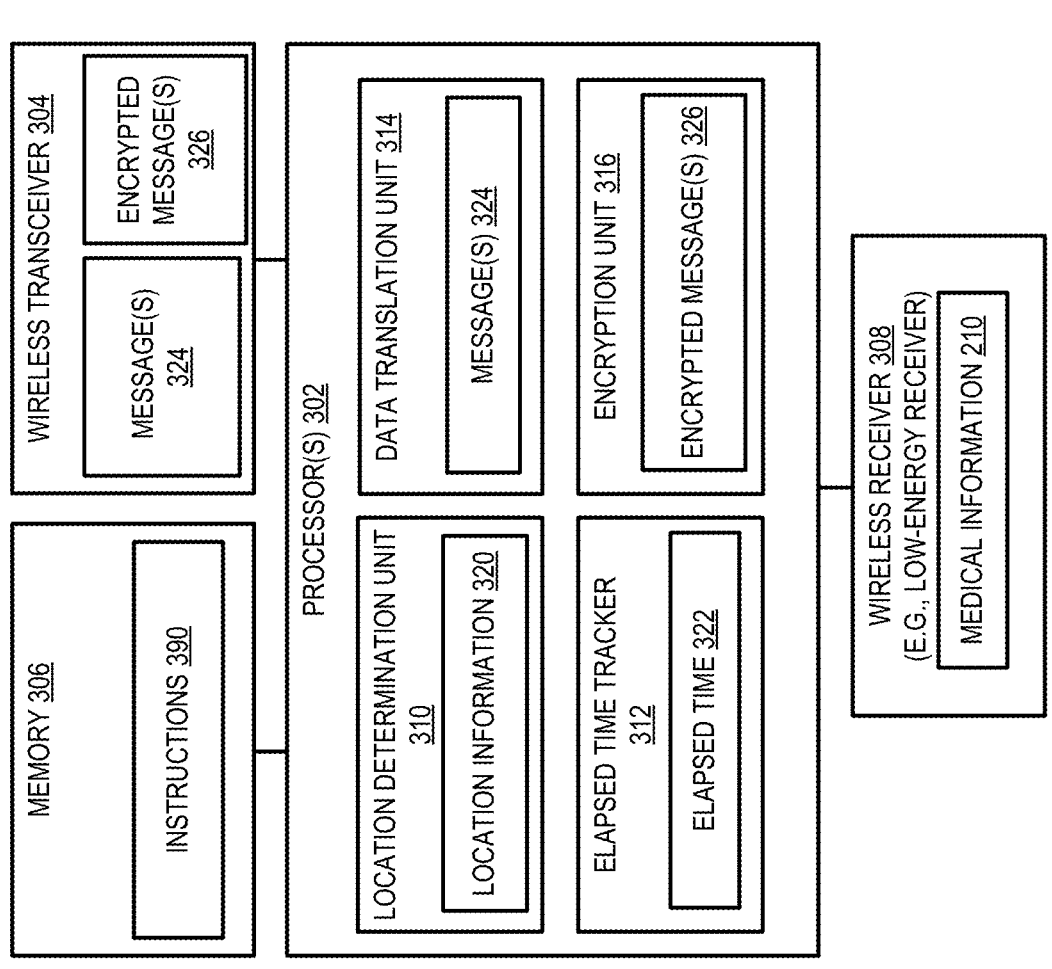
*FIG. 3*

500

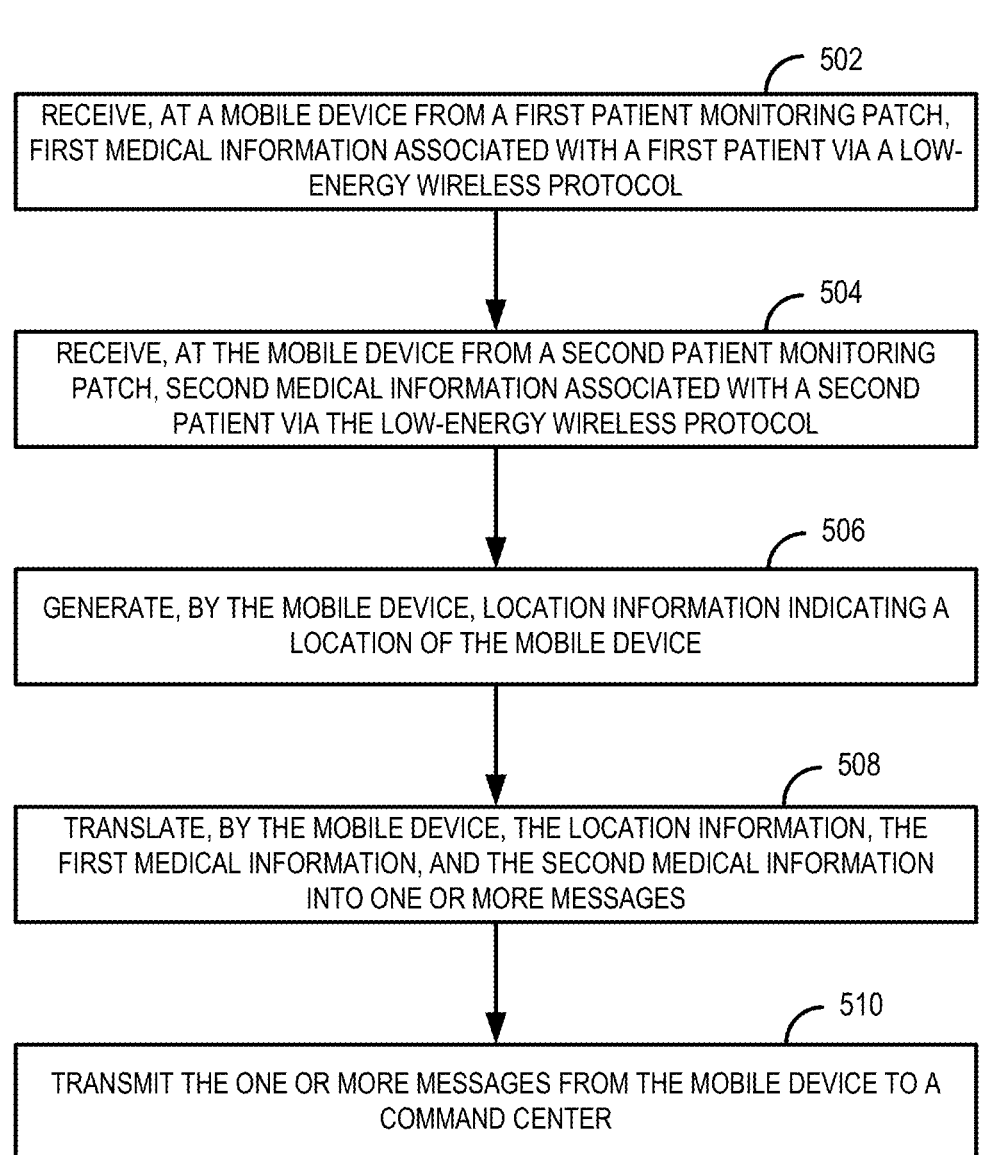

502

RECEIVE, AT A MOBILE DEVICE FROM A FIRST PATIENT MONITORING PATCH, FIRST MEDICAL INFORMATION ASSOCIATED WITH A FIRST PATIENT VIA A LOW-ENERGY WIRELESS PROTOCOL

504

RECEIVE, AT THE MOBILE DEVICE FROM A SECOND PATIENT MONITORING PATCH, SECOND MEDICAL INFORMATION ASSOCIATED WITH A SECOND PATIENT VIA THE LOW-ENERGY WIRELESS PROTOCOL

506

GENERATE, BY THE MOBILE DEVICE, LOCATION INFORMATION INDICATING A LOCATION OF THE MOBILE DEVICE

508

TRANSLATE, BY THE MOBILE DEVICE, THE LOCATION INFORMATION, THE FIRST MEDICAL INFORMATION, AND THE SECOND MEDICAL INFORMATION INTO ONE OR MORE MESSAGES

510

TRANSMIT THE ONE OR MORE MESSAGES FROM THE MOBILE DEVICE TO A COMMAND CENTER

*FIG. 5*

PATIENT MONITORING PATCH

FIELD OF THE DISCLOSURE

The subject disclosure is generally related to monitoring a patient.

BACKGROUND

When a patient needs medical attention after suffering an injury, such as an injury from an accident, first responders typically meet the patient at the scene of the accident. First responders can perform a preliminary medical evaluation on the patient. As non-limiting examples, first responders can perform a preliminary diagnosis of the injury, measure the patient's heart-rate, take the patient's temperature, etc. After the first responders perform the preliminary medical evaluation, the first responders can provide preliminary treatment or emergency care for the patient while the patient is in route to a care facility, such as a hospital.

Typically, the care facility that is going to accept the patient uses voice calls over radio to communicate with a central dispatch associated with the first responders. Using the voice calls over radio, the care facility can receive a summary of the patient's status prior to the patient arriving at the care facility. However, in some scenarios, data regarding the patient's status can be miscommunicated. Regardless of whether the data is miscommunicated, the care facility typically does not receive a detailed and current status of the patient until the patient arrives at the care facility and is handed over to staff at the care facility. As a result, time that could otherwise be used treating the patient at the care facility is used to determine the detailed and current status of the patient.

SUMMARY

In a particular implementation, a device for monitoring a patient includes a substrate, an adhesive layer coupled to a first side of the substrate, and a circuit board coupled to a second side of the substrate. The adhesive layer is configured to adhere to a patient. The device also includes a plurality of switches coupled to the circuit board. Each switch of the plurality of switches is associated with a respective condition and is switchable by a user between a first state indicating that a corresponding condition is believed to be associated with the patient and a second state indicating that the corresponding condition is not believed to be associated with the patient. The device also includes a wireless transmitter coupled to the circuit board. The wireless transmitter is configured to transmit medical information associated with the patient to a mobile device. The medical information includes data indicating a setting of each of the plurality of switches.

In another particular implementation, a system includes a first patient monitoring patch configured to transmit first medical information associated with a first patient to a mobile device via a low-energy wireless protocol. The system also includes a second patient monitoring patch configured to transmit second medical information associated with a second patient to the mobile device via the low-energy wireless protocol. The system further includes the mobile device. The mobile device is configured to generate location information indicating a location of the mobile device. The mobile device is further configured to translate the location information, the first medical information, and the second medical information into one or more messages. The mobile device is also configured to transmit the one or more messages to a command center.

In another particular implementation, a method includes receiving, at a mobile device from a first patient monitoring patch, first medical information associated with a first patient via a low-energy wireless protocol. The method also includes receiving, at the mobile device from a second patient monitoring patch, second medical information associated with a second patient via the low-energy wireless protocol. The method further includes generating, by the mobile device, location information indicating a location of the mobile device. The method further includes translating, by the mobile device, the location information, the first medical information, and the second medical information into one or more messages. The method also includes transmitting the one or more messages from the mobile device to a command center.

The features, functions, and advantages described herein can be achieved independently in various implementations or can be combined in yet other implementations, further details of which can be found with reference to the following description and drawings.

BRIEF DESCRIPTION OF THE DRAWINGS

FIG. 3 is a diagram that illustrates an example of a mobile device configured to process data from a patient monitoring patch.

FIG. 5 is a flowchart of an example of a method of monitoring a status of multiple patients using patient monitoring patches.

DETAILED DESCRIPTION

Figure 1:
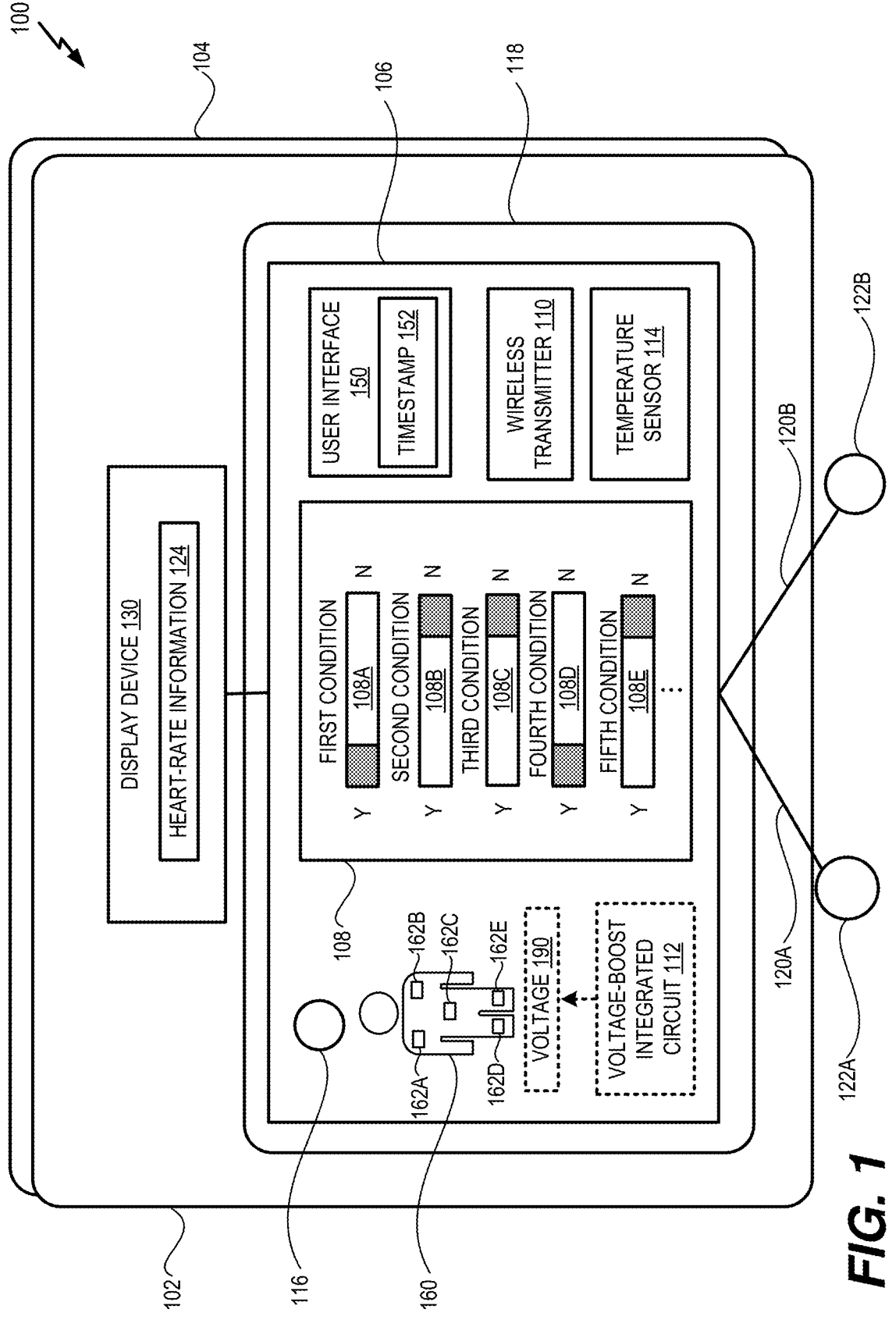
FIG. 1 is a diagram that illustrates an example of a patient monitoring patch configured to collect patient vital signs and transmit corresponding medical information to a mobile device.

Aspects disclosed herein present example systems and methods for monitoring a status of a patient by attaching a wearable patch to the patient. For example, a relatively small wearable patch can be attached to a chest of the patient by a user, such as a first responder on a scene of an accident. The wearable patch includes a plurality of switches that are switchable between a first state and a second state to identify different conditions believed to be experienced by the patient. The first state can indicate that the patient is believed to have a condition associated with a corresponding switch, and the second state can indicate that the patient is not believed to have the condition associated with the corresponding switch. As non-limiting examples, the plurality of switches can include a switch indicating whether the patient has an altered mental state, a switch indicating whether the patient has a puncture, a switch indicating whether the patient has a gunshot injury, a switch indicating whether the patient has a burn injury, a switch indicating whether the patient has a blunt force trauma injury, etc. The user can set each switch to either the first state or the second state based on initial observations. The wearable patch can also include different sensors that are usable to measure the patient's vital signs. As non-limiting examples, the wearable patch can include heart-rate electrodes configured to measure electrical activity associated with the patient's heart, a temperature sensor configured to measure the patient's body temperature, a breathing monitor configured to measure the patient's oxygen level and respiration rate, etc.

Based on the settings of each switch and the measurements from the sensors, patient data can be collected by the wearable patch and transmitted to a nearby mobile device using a low-energy wireless protocol, such as a Bluetooth® Low Energy (BLE) protocol (Bluetooth® is a registered trademark of Bluetooth SIG, Inc., Washington). However, it should be understood that the BLE protocol is merely a non-limiting example of a low-energy wireless protocol and other protocols can be used in conjunction with the techniques described herein. For example, protocols that are not marketed or considered to be "low-energy" can correspond to a protocol used in conjunction with the techniques described herein if the power consumption associated with the protocol is below a particular threshold level, such as one watt. As used herein, a "low-energy wireless protocol" or a "low-energy protocol" can correspond to a protocol that supports low-bandwidth communications between devices using a relatively low amount of power. As a non-limiting example, a device can experience a power consumption of approximately ten milliwatts to communicate data using a low-energy wireless protocol. However, in other examples, the device can experience a lower power consumption or a higher power consumption.

The mobile device can translate the patient data into one or more messages and send the messages to a command center, such as a central dispatch service or a care facility center, to provide updates regarding the patient's condition. The wearable patch can periodically or occasionally measure the patient's vital signs and send updated patient data to the mobile device to enable the mobile device to transmit updated messages to the command center. As a result, a detailed and current status of the patient can be obtained by a receiving care facility prior to the patient's arrival. Additionally, miscommunication of the patient data is highly unlikely, as the patient data is communicated using the wearable patch as opposed to using voice calls over radio.

According to some scenarios, the mobile device can be associated with specialized networks. As a non-limiting example, the mobile device can be associated with a care facility network or communication system, such as FIRST-NET, that enables the mobile device to send messages to (and receive messages from) a hospital dispatch center. According to this example, the translated patient data from the wearable patch can be transmitted by the mobile device using FIRSTNET. As another non-limiting example, the mobile device can be associated with an armed services network or communication system, such as a blue force tracking network, that enables the mobile device to send messages to (and receive messages from) an armed services care team.

The figures and the following description illustrate specific exemplary embodiments. It will be appreciated that those skilled in the art will be able to devise various arrangements that, although not explicitly described or shown herein, embody the principles described herein and are included within the scope of the claims that follow this description. Furthermore, any examples described herein are intended to aid in understanding the principles of the disclosure and are to be construed as being without limitation. As a result, this disclosure is not limited to the specific embodiments or examples described below, but by the claims and their equivalents.

Particular implementations are described herein with reference to the drawings. In the description, common features are designated by common reference numbers throughout the drawings. In some drawings, multiple instances of a particular type of feature are used. Although these features are physically and/or logically distinct, the same reference number is used for each, and the different instances are distinguished by addition of a letter to the reference number. When the features as a group or a type are referred to herein (e.g., when no particular one of the features is being referenced), the reference number is used without a distinguishing letter. However, when one particular feature of multiple features of the same type is referred to herein, the reference number is used with the distinguishing letter. For example, referring to FIG. 1, multiple switches are illustrated and associated with reference numbers 108A, 108B, 108C, 108D, and 108E. When referring to a particular one of these switches, such as the switch 108A, the distinguishing letter "A" is used. However, when referring to any arbitrary one of these switches or to these switches as a group, the reference number 108 is used without a distinguishing letter.

As used herein, various terminology is used for the purpose of describing particular implementations only and is not intended to be limiting. For example, the singular forms "a," "an," and "the" are intended to include the plural forms as well, unless the context clearly indicates otherwise. Further, some features described herein are singular in some implementations and plural in other implementations. To illustrate, FIG. 3 depicts a mobile device 300 with one or more processors ("processor(s)" 302 in FIG. 3), which indicates that in some implementations the mobile device 300 includes a single processor 302 and in other implementations the mobile device 300 includes multiple processors 302. For ease of reference herein, such features are generally introduced as "one or more" features and are subsequently referred to in the singular unless aspects related to multiple of the features are being described.

The terms "comprise," "comprises," and "comprising" are used interchangeably with "include," "includes," or "including." Additionally, the term "wherein" is used interchangeably with the term "where." As used herein, "exemplary" indicates an example, an implementation, and/or an aspect, and should not be construed as limiting or as indicating a preference or a preferred implementation. As used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). As used herein, the term "set" refers to a grouping of one or more elements, and the term "plurality" refers to multiple elements.

As used herein, "generating," "calculating," "using," "selecting," "accessing," and "determining" are interchangeable unless context indicates otherwise. For example, "generating," "calculating," or "determining" a parameter (or a signal) can refer to actively generating, calculating, or determining the parameter (or the signal) or can refer to using, selecting, or accessing the parameter (or signal) that is already generated, such as by another component or device. As used herein, "coupled" can include "communicatively coupled," "electrically coupled," or "physically coupled," and can also (or alternatively) include any combinations thereof. Two devices (or components) can be coupled (e.g., communicatively coupled, electrically coupled, or physically coupled) directly or indirectly via one or more other devices, components, wires, buses, networks (e.g., a wired network, a wireless network, or a combination thereof), etc. Two devices (or components) that are electrically coupled can be included in the same device or in different devices and can be connected via electronics, one or more connectors, or inductive coupling, as illustrative, non-limiting examples. In some implementations, two devices (or components) that are communicatively coupled, such as in electrical communication, can send and receive electrical signals (digital signals or analog signals) directly or indirectly, such as via one or more wires, buses, networks, etc. As used herein, "directly coupled" is used to describe two devices that are coupled (e.g., communicatively coupled, electrically coupled, or physically coupled) without intervening components.

FIG. 1 depicts an example of a patient monitoring patch 100 configured to collect patient vital signs and transmit corresponding medical information to a mobile device. The patient monitoring patch 100 can be a relatively small wearable patch that is deployed with a medical adhesive on a chest of a patient. As detailed below, the patient monitoring patch 100 can be used in a variety of different scenarios. As non-limiting examples, the patient monitoring patch 100 can be used by emergency personnel arriving on a scene of an accident, military personnel responding to combat injuries and casualties on a battlefield, etc.

The patient monitoring patch 100 can include a substrate 102 and an adhesive layer 104 coupled to a first side of the substrate 102. For example, the adhesive layer 104 can be coupled to a back side of the substrate 102. The adhesive layer 104 can be configured to adhere to a patient. According to one implementation, the adhesive layer 104 is comprised of a medical-grade adhesive, such as a hydrocolloid adhesive, that is configured to adhere to a chest of the patient. The substrate 102 may be comprised of a flexible material, such as plastic, that is durable and relatively light in weight.

The patient monitoring patch 100 can also include a circuit board 106 that is coupled to a second side of the substrate 102. For example, the circuit board 106 can be coupled to a front side of the substrate 102. According to one implementation, the circuit board 106 corresponds to a printed circuit board that is injected in the substrate 102. According to one implementation, the circuit board 106 includes a flexible circuit or a flexible circuit board. As a non-limiting example, the circuit board 106 may include or correspond to a thin insulating polymer film having conductive circuit patterns and can be supplied with a thin polymer coating to protect conductive circuits. As illustrated in FIG. 1, a battery 118 can be coupled to the circuit board 106 to provide power to the circuit board 106. According to one implementation, the battery 118 can be a button cell battery (or a flexible battery) that provides a voltage 190 to the circuit board 106. For example, the voltage 190 provided by the battery 118 can range between three volts and five volts. According to one implementation, the patient monitoring patch 100 includes a voltage-boost integrated circuit 112 that is coupled to the battery 118 and to the circuit board 106. The voltage-boost integrated circuit 112 can be configured to regulate the voltage 190 to the circuit board 106. As a non-limiting example, the voltage-boost integrated circuit 112 can regulate the voltage 190 such that the voltage 190 provided to the circuit board 106 is five volts.

In the illustrated example of FIG. 1, the patient monitoring patch 100 also includes an activation device 116 that can be configured to activate the circuit board 106 via battery power associated with the battery 118. According to one implementation, the activation device 116 can include a switch that, when switched to an "activate" position, enables battery power associated with the battery 118 to be provided to power the circuit board 106. According to another implementation, the activation device 116 can include a button that, when pressed, enables battery power associated with the battery 118 to be provided to power the circuit board 106. According to yet another implementation, the activation device 116 can include a pull tab that, when pulled, enables battery power associated with the battery 118 to be provided to power the circuit board 106. It should be understood that the above examples are not intended to be limiting and other activation devices can be integrated into the patient monitoring patch 100.

As illustrated in FIG. 1, a plurality of switches 108 is coupled to the circuit board 106. Each switch 108A-108E of the plurality of switches can be associated with a respective condition (e.g., patient condition, health condition, diagnosis, etc.). As non-limiting examples, a first switch 108A can be associated with a first condition that indicates whether the patient has an altered mental state (e.g., an unconscious mental state), a second switch 108B can be associated with a second condition that indicates whether the patient has a puncture, a third switch 108C can be associated with a third condition that indicates whether the patient has a burn injury, a fourth switch 108D can be associated with a fourth condition that indicates whether the patient has a gunshot injury, a fifth switch 108E can be associated with a fifth condition that indicates whether the patient has a blunt force trauma injury, etc. Although five switches 108A-108E and five corresponding conditions are described, in other implementations, additional switches and corresponding conditions can be included in the plurality of switches 108. In other implementations, the plurality of switches 108 can include fewer switches or may be associated with different conditions. As a non-limiting example, in other implementations, the plurality of switches 108 can include two (or more) switches.

According to some implementations, the switches 108 can be ordered or arranged based on a medical evaluation criterion. As a non-limiting example, switches 108 associated with critical medical conditions can be placed above switches 108 associated with less critical medical conditions. As a result, a user operating the switches 108 can set the switches 108 associated with the critical medical conditions prior to setting the switches 108 associated with the less critical medical conditions.

Each switch 108A-108E is switchable by a user between a first state (Y) indicating that a corresponding condition is believed to be associated with the patient and a second state (N) indicating that the corresponding condition is not believed to be associated with the patient. For example, according to the above-described examples, the first switch 108A indicates whether the patient has an altered mental state. Upon attaching the patient monitoring patch 100 to the patient, the user can access the patient to determine whether the patient has an altered mental state. If the user determines the patient has an altered mental state, the user can set the first switch 108A to the first state (Y). However, if the user determines that the patient does not have an altered mental state, the user can set the first switch 108A to the second state (N). Similar assessments and actions can be performed by the user to set the other switches 108A-108E. According to one implementation, the switches 108A-108E can include dip switches that are easily settable by the user. According to other implementations, the switches 108A-108E can be physical switches that have other configurations. As non-limiting examples, the switches 108A-108E can include rotary switches, push button switches, etc. By using physical switches 108A-108E, as opposed to digital switches, in stressful situations or situations in which the user is wearing gloves, the physical switches 108A-108E can easily be set by the user.

The conditions for the switches 108A-108E can be conditions that are readily identifiable by a user, such as an emergency responder. For example, according to the above-described conditions, an emergency responder can quickly determine which conditions are applicable to the patient and set each switch 108A-108E based on the determination. As described below, the setting of each switch 108A-108E is used to relay information about the patient to a third party, such as a hospital.

According to some implementations, each switch 108A-108E could be switchable to a third state (e.g., a default state) in between the first state (Y) and the second state (N). For example, if a switch 108 is in the third state, it can indicate that an evaluation for a corresponding condition has yet to be performed. Thus, a switch 108 set to the third state can act as a prompt to the user to perform a corresponding condition evaluation.

According to some implementations, the patient monitoring patch 100 can also include other input devices, such as an input to designate one or more areas of the patient's body that are associated with a particular condition or injury. To illustrate, an input device may include an outline 160 of a human body coupled to the circuit board 106. According to one example, the outline 160 can be etched into the circuit board 106. According to another example, the outline 160 can be comprised of a nonconductive material, such as plastic, that is attached to the circuit board 106 using an adhesive. Within the outline 160, a plurality of light emitting diode (LED) buttons 162A-162E can coupled to the circuit board 106. Each LED button 162A-162E can be selectively activated by a user to indicate a location of an injury to the patient. As illustrated in FIG. 1, an LED button 162A can be coupled to the circuit board 106 at a location within the outline 160 indicative of a right arm location, an LED button 162B can be coupled to the circuit board 106 at a location within the outline 160 indicative of a left arm location, an LED button 162C can be coupled to the circuit board 106 at a location within the outline 160 indicative of a mid-section location, an LED button 162D can be coupled to the circuit board 106 at a location within the outline 160 indicative of a right leg location, and an LED button 162E can be coupled to the circuit board 106 at a location within the outline 160 indicative of a left leg location. It should be understood that the locations of the LED buttons 162 illustrated in FIG. 1 are merely for illustrative purposes and should not be construed as limiting. In other implementations, the LED buttons 162 can be coupled to the circuit board 106 at different locations within the outline 160. Additionally, in other locations, additional (or fewer) LED buttons 162 can be coupled to the circuit board 106 within the outline 160.

Upon a preliminary evaluation of the patient, the user may selectively activate LED buttons 162 at areas within the outline 160 that are indicative of injury areas believed to be suffered by the patient. As a non-limiting example, if the user evaluates the patient and believes that the patient is suffering from a gunshot wound in the patient's right arm, the user can activate the LED button 162A. In response to activating the LED button 162A, the patient monitoring patch 100 can generate data indicating a believed location of the injury. Thus, according to the examples described above, the user can set the fourth switch 108D to the first state (Y) to indicate that the patient is believed to suffer from a gunshot injury and the user can activate the LED button 162A to indicate the location of the gunshot injury. It should be understood that although LED buttons 162 are illustrated, in other implementations, different mechanisms can be used to indicate the location of the injury. As a non-limiting example, the location of the injury can be indicated by activating push button switches.

The patient monitoring patch 100 also includes a first lead 120A extending from the circuit board 106 to a first heart-rate electrode 122A attachable to the patient and a second lead 120B extending from the circuit board 106 to a second heart-rate electrode 122B attachable to the patient. The heart-rate electrodes 122A, 122B can be placed at different areas of the patient's body, such as the chest and abdomen, to measure electrical activity associated with the patient's heart. Thus, the heart-rate electrodes 122A, 122B can detect heart-rate information 124 (e.g., the electrical activity) associated with the patient and provide the heart-rate information 124, via the leads 120A, 120B, to the one or more components, circuits, or devices associated with the circuit board 106.

In the example illustrated in FIG. 1, the patient monitoring patch 100 also includes a display device 130 coupled to the circuit board 106. The display device 130 can be configured to display the heart-rate information 124 detected by the heart-rate electrodes 122A, 122B. To illustrate, the display device 130 can include a plurality of light-emitting diodes (LEDs) that are used to display the patient's heart-rate. It should be understood that the display device 130 can be used to display other information detected by components of the patient monitoring patch 100. As non-limiting examples, the display device 130 can display a measured oxygen level, a measured respiratory rate, a timestamp indicating an amount of elapsed time since the patient was injured, etc. According to some implementations, the display device 130 can display a prompt to reevaluate the patient.

Additional components can be coupled to the circuit board 106 to collect additional information about the patient. For example, according to one implementation, the patient monitoring patch 100 can also include a temperature sensor 114 coupled to the circuit board 106. The temperature sensor 114 can be configured to detect a temperature of the patient. According to another implementation, the patient monitoring patch 100 can include a breathing monitor (not shown) or oxygen sensor (not shown) coupled to the circuit board. In this implementation, the breathing monitor or oxygen sensor can be configured to measure oxygen levels, respiratory rate, or another lung function associated with the patient.

As another example, according to one implementation, the patient monitoring patch 100 can also include a user interface 150 coupled to the circuit board 106. The user interface 150 can be configured to receive a user input indicating a timestamp 152. The timestamp 152 can indicate an elapsed time between an injury associated with the patient and application of the patient monitoring patch 100. As a non-limiting illustrative example, based on the switches 108A, 108D set to the first state (Y) and the example conditions described above, the patient is believed to have experienced a gunshot wound and is in an altered mental state. The user (e.g., the emergency responder) that applies the patient monitoring patch 100 to the patient can use the user interface 150 to indicate an elapsed time (or an estimated elapsed time) since the gunshot injury. As described below, a mobile device can use the timestamp 152 indicated by the user to track how much time has elapsed since the patient sustained the injury. Although the user interface 150 is illustrated as a component of the circuit board 106, in other implementations, the user interface 150 can be integrated into other components. As a non-limiting example, the user interface 150 can be integrated into the display device 130.

The patient monitoring patch 100 also includes a wireless transmitter 110 coupled to the circuit board 106. The wireless transmitter 110 can be configured to transmit medical information to a mobile device. As described in greater detail with respect to FIG. 2, the medical information transmitted by the wireless transmitter 110 can include data indicating a setting of each switch 108A-108E, data indicating electrical activity of the patient's heart, data indicating the patient's temperature, data indicating an elapsed time since the patient's injury, and other data used to diagnose and treat the patient. According to one implementation, the wireless transmitter 110 can include a low-energy wireless transmitter. For example, the wireless transmitter 110 can transmit data via a low-energy wireless protocol, such as a Bluetooth Low Energy (BLE) protocol. According to some implementations, short-range low-energy wireless transmitters can transmit data using between 0.5 milliwatts and 10 milliwatts of power while high-energy wireless transmitters typically use at least one watt of power to transmit data. According to some implementations, long-range low-energy wireless transmitters can transmit data using up to 100 milliwatts of power, but can average between 15 milliwatts and 20 milliwatts of total power consumption. Each patient monitoring patch 100 can include a low energy wireless transmitter 110, which can be configured to read and/or receive periodic input of measurements of the patient's vital signs, and/or configured for intermittent or periodic transmission of updated patient data to prolong battery life and monitoring patch operation. One example of a low energy wireless transmitter 110 could be a Bluetooth Low Energy nRF52811 transceiver module sold by TE Connectivity. Additionally, transmissions by the wireless transmitter 110 of each monitoring patch 100 can be at a periodic time interval unique to each monitoring patch 100 to stagger transmissions and avoid collision of patch signals (e.g., periodic transmissions may occur at an interval determined based on each patch's unique ID).

The patient monitoring patch 100 of FIG. 1 enables a user (e.g., a first responder) to monitor the health and status of a patient without the use of typical infrastructures that may be burdensome, such as an ambulance's support infrastructure. As a result, relatively inexperienced or untrained first responders can obtain a patient's status by applying the patient monitoring patch 100. Additionally, in scenarios in which the patient is believed to have a high infectious disease, by applying the patient monitoring patch 100 to the patient, first responders can obtain vital information about the patient while reducing extended periods of contact with the patient. It should also be appreciated that patient monitoring patch 100 may enable non-medical professionals to assist medical professionals in obtaining the patient's status. As a non-limiting example, if police arrive on the scene of an accident prior to emergency medical services, police can apply the patient monitoring patch 100 to obtain the medical status of the patient.

It should also be appreciated that the patient monitoring patch 100 can be a relatively low-cost solution to monitoring a health status of a patient. As a result, the patient monitoring patch 100 can be a disposable (or single use) patch that is convenient to use in a wide variety of contexts. For example, as described above, that patient monitoring patch 100 can be used in civilian scenarios in which a civilian is injured and emergency medical personnel evaluate the civilian. However, the patient monitoring patch 100 can also be used in military or battlefield scenarios. For example, a soldier can pack multiple patches 100 and attach the patches 100 to wounded soldiers on the battlefield. As a result, the status of multiple wounded soldiers can quickly be obtained using the patches 100.

Figure 2:
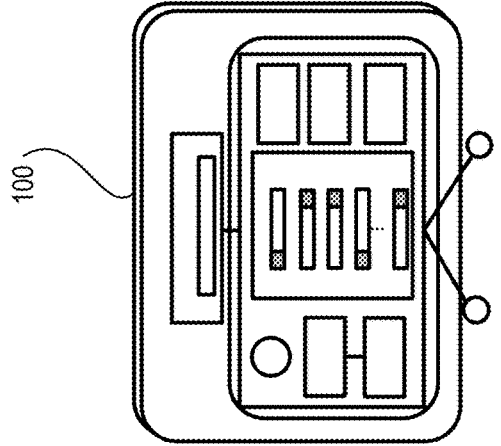
FIG. 2 is a diagram that illustrates an example of a system configured to transfer medical information from a patient monitoring patch to a mobile device.

FIG. 2 depicts an example of a system 200 configured to transfer medical information from a patient monitoring patch to a mobile device. The system 200 includes the patient monitoring patch 100 of FIG. 1 and a mobile device 300. The mobile device 300 can include a mobile phone, a laptop, a portable digital assistant (PDA), a specialized medical device, or any other mobile device that has capabilities to receive information and transmit information. The patient monitoring patch 100 can be configured to transmit medical information 210 to the mobile device 300 via a low-energy wireless protocol 290, such as a BLE protocol. For example, the wireless transmitter 110 of the patient monitoring patch 100 can transmit the medical information 210 to the mobile device 300 via the low-energy wireless protocol 290.

The medical information 210 can include a patient monitoring patch identification number 220 associated with the patient monitoring patch 100. For example, the patient monitoring patch 100 can include a serial number (e.g., the patient monitoring patch identification number 220) that distinguishes the patient monitoring patch 100 from other patient monitoring patches. In scenarios in which the patient monitoring patch 100 is a disposable patch that is included in a packet of patches, the patient monitoring patch identification number 220 can be used by the mobile device 300 to identify the patient monitoring patch 100, and the corresponding patient, from other patches in the packet. The patient monitoring patch identification number 220 may also be used to pair the mobile device 300 with the patient monitoring patch 100 so that the mobile device 300 can receive the medical information 210 via the low-energy wireless protocol 290.

Thus, each patient monitoring patch 100 can include a unique identification number 220 that can be used to distinguish between other patient monitoring patches 100. As a result, once a particular patient monitoring patch 100 is attached to a particular patient, the unique identification number 220 of the particular patient monitoring patch 100 can be used to track a health history (e.g., condition changes, heart-rate trends, etc.) of the particular patient. Additionally, by tracking the history using the unique identification number 220, as opposed to using patient identifying information (e.g., a patient name or date of birth), patient confidentiality concerns can be alleviated.

The medical information 210 can also include the heart-rate information 124 detected by the heart-rate electrodes 122A, 122B. For example, the medical information 210 can include data that indicates electrical activity associated with the patient's heart, as detected by the heart-rate electrodes 122A, 122B. The medical information 210 can also include the timestamp 152 indicating the elapsed time between the injury associated with the patient and application of the patient monitoring patch 100. As described with respect to FIG. 3, the mobile device 300 can use the timestamp 152 to track how much time has elapsed since the patient sustained the injury.

The medical information 210 can also include condition statuses 208 indicated by settings of the switches 108. For example, the medical information 210 can include data indicating a first condition status 208A of the patient. The first condition status 208A can be associated with a setting of the first switch 108A. To illustrate, in the illustrative example of FIG. 1, the first switch 108A is set to the first state (Y) indicating that the patient has an altered mental state. As a result, the first condition status 208A can include data indicating that the patient has an altered mental state. As another example, the medical information 210 can include data indicating a second condition status 208B of the patient. The second condition status 208B can be associated with a setting of the second switch 108B. To illustrate, in the illustrative example of FIG. 1, the second switch 108B is set to the second state (N) indicating that the patient does not have a puncture. As a result, the second condition status 208B can include data indicating that the patient does not have a puncture.

As another example, the medical information 210 can include data indicating a third condition status 208C of the patient. The third condition status 208C can be associated with a setting of the third switch 108C. To illustrate, in the illustrative example of FIG. 1, the third switch 108C is set to the second state (N) indicating that the patient does not have a burn injury. As a result, the third condition status 208C can include data indicating that the patient does not have a burn injury. As another example, the medical information 210 can include data indicating a fourth condition status 208D of the patient. The fourth condition status 208D can be associated with a setting of the fourth switch 108D. To illustrate, in the illustrative example of FIG. 1, the fourth switch 108D is set to the first state (Y) indicating that the patient has a gunshot injury. As a result, the fourth condition status 208D can include data indicating that the patient has a gunshot injury. As another example, the medical information 210 can include data indicating a fifth condition status 208E of the patient. The fifth condition status 208E can be associated with a setting of the fifth switch 108E. To illustrate, in the illustrative example of FIG. 1, the fifth switch 108E is set to the second state (N) indicating that the patient does not have a blunt force trauma injury. As a result, the fifth condition status 208E can include data indicating that the patient does not have a blunt force trauma injury.

According to some implementations, the medical information 210 can also include temperature data 222 indicative of the patient temperature detected by the temperature sensor 114. According to other implementations, the medical information 210 can include additional data 224 that indicates a condition of the patient. As non-limiting examples, the additional data 224 can include additional condition statuses associated with other switches in the plurality of switches 108, data associated with the patient's breathing or lung function, etc.

The mobile device 300 can receive the medical information 210 from the patient monitoring patch 100 via the low-energy wireless protocol 290. As described in greater detail with respect to FIGS. 3-4, the mobile device 300 can process and translate the data associated with the medical information 210 into one or more messages that are sent to a third party, such as a hospital, a central dispatch service, or a command center.

The techniques described with respect to FIG. 2 enable the patient monitoring patch 100 to connect with the mobile device 300 (e.g., a mobile device of a first responder) via the low-energy wireless protocol 290. For example, the unique identification number 220 of the patient monitoring patch 100 can be paired with the mobile device 300 to establish a connection. As a result, the medical information 210 can be transmitted from the patient monitoring patch 100 to the mobile device 300 using a relatively small amount of transfer power, which conserves battery power at the patient monitoring patch 100.

FIG. 3 depicts an example of the mobile device 300 configured to process data from the patient monitoring patch 100. For example, the mobile device 300 is operable to receive the medical information 210 from the patient monitoring patch 100, translate the data in the medical information 210 into messages, and communicate the messages to a third party, such as a care facility, a central dispatch service, or a command center, to facilitate improved care for the patient. According to some implementations, the mobile device 300 can be a standalone device, such as a mobile phone, a laptop computer, etc. According to some implementations, the mobile device 300 can be onboard or integrated within a response vehicle, such as an ambulance or a troop transport vehicle. In some scenarios, a standalone mobile device can handoff communications with the patient monitoring patch 100 to a nearby response vehicle or relay communications to the response vehicle.

The mobile device 300 includes one or more processors 302, a wireless transceiver 304 coupled to the one or more processors 302, a memory 306 coupled to the one or more processors 302, and a wireless receiver 308 coupled to the one or more processors 302. The memory 306 can include a non-transitory storage medium that includes instructions 390 that are executable by the one or more processors 302 to perform the operations described herein.

The wireless receiver 308 can be configured to receive the medical information 210 from the patient monitoring patch 100. To illustrate, the wireless receiver 308 may correspond to a low-energy receiver that receives the medical information 210 via the low-energy wireless protocol 290. According to some implementations, low-energy wireless receivers can receive data using approximately ten milliwatts of power while high-energy wireless receivers typically use at least one watt of power to receive data. The mobile device 300 can be within a relatively close proximity (e.g., within one-hundred fifty feet) of the patient monitoring patch 100 to enable the transfer of the medical information 210 using the low-energy wireless protocol 290. As described below, the close proximity between the mobile device 300 and the patient monitoring patch 100 enables the mobile device 300 to use the location of the mobile device 300 as the location of the patient monitoring patch 100.

The one or more processors 302 include a location determination unit 310, an elapsed time tracker 312, a data translation unit 314, an encryption unit 316, or a combination thereof. According to some implementations, one or more of the components of the one or more processors 302 can be implemented using dedicated hardware circuitry, such as an application-specific integrated circuit (ASIC) or a field programmable gate array (FPGA). According to some implementations, one or more of the components of the one or more processors 302 can be implemented by executing the instructions 390 stored in the memory 306.

The location determination unit 310 can be configured to determine a location of the mobile device 300 and generate corresponding location information 320 of the mobile device 300. As a non-limiting example, the location determination unit 310 can access or include a Global Positioning System (GPS) to determine the location of the mobile device 300. Based on the determined location, the location determination unit 310 can generate the location information 320 indicating the location of the mobile device 300. Because the medical information 210 is transmitted to the mobile device 300 via the low-energy wireless protocol 290, the patient monitoring patch 100 remains relatively close in proximity to the mobile device 300 during use. As a result, the mobile device 300 can use its own location as the location of the patient monitoring patch 100 or can estimate the location of the patient monitoring patch 100 based on its own location.

The elapsed time tracker 312 can be configured to track an elapsed time 322 since the injury associated with the patient. For example, the elapsed time tracker 312 can access the timestamp 152 from the medical information 210 to determine the elapsed time between the injury and application of the patient monitoring patch 100. Based on the timestamp 152, the elapsed time tracker 312 can track the elapsed time 322 since the injury. For example, the elapsed time tracker 312 can incrementally count (or track) time as time elapses.

The data translation unit 314 can be configured to translate the location information 320, the elapsed time 322, and the medical information 210 into one or more messages 324. For example, the location information 320, the elapsed time 322, and the medical information 210 can have a data format that is not readily understandable to a user. The data translation unit 314 can translate the data to a format that is readily understandable to users, such as a standard language format, and generate one or more messages (e.g., text messages) having the corresponding information in the standard language format. According to some implementations, the encryption unit 316 can encrypt the one or more messages 324 to generate one or more encrypted messages 326.

The wireless transceiver 304 can be configured to transmit the one or more messages 324 (or the one or more encrypted messages 326) to a third party, such as a command center, a central dispatch service, a care facility, etc. According to one implementation, the one or more messages 324 are transmitted using a cellular communication protocol or a satellite communication protocol. That is, the one or more messages 324 can be transmitted using a protocol and corresponding hardware that consume more power than the low-energy wireless protocol 290 used to transmit the medical information 210. According to another implementation, the one or more messages 324 are transmitted using a wireless communication protocol. In some scenarios, specialized networks can be used to transmit the one or more messages 324. As a non-limiting example, the one or more messages 324 can be transmitted via a FIRSTNET network. As another non-limiting example, the one or more messages 324 can be transmitted via a blue force tracking network.

Thus, the operations of the mobile device 300 of FIG. 3 can be used to reduce miscommunication that may result from voice calls over radio. For example, by translating the medical information 210 from the patient monitoring patch 100 into the messages 324 and sending the messages 324 to a third party, the mobile device 300 can reduce or eliminate human error associated with communicating patient information via voice calls over radio.

Figure 4:
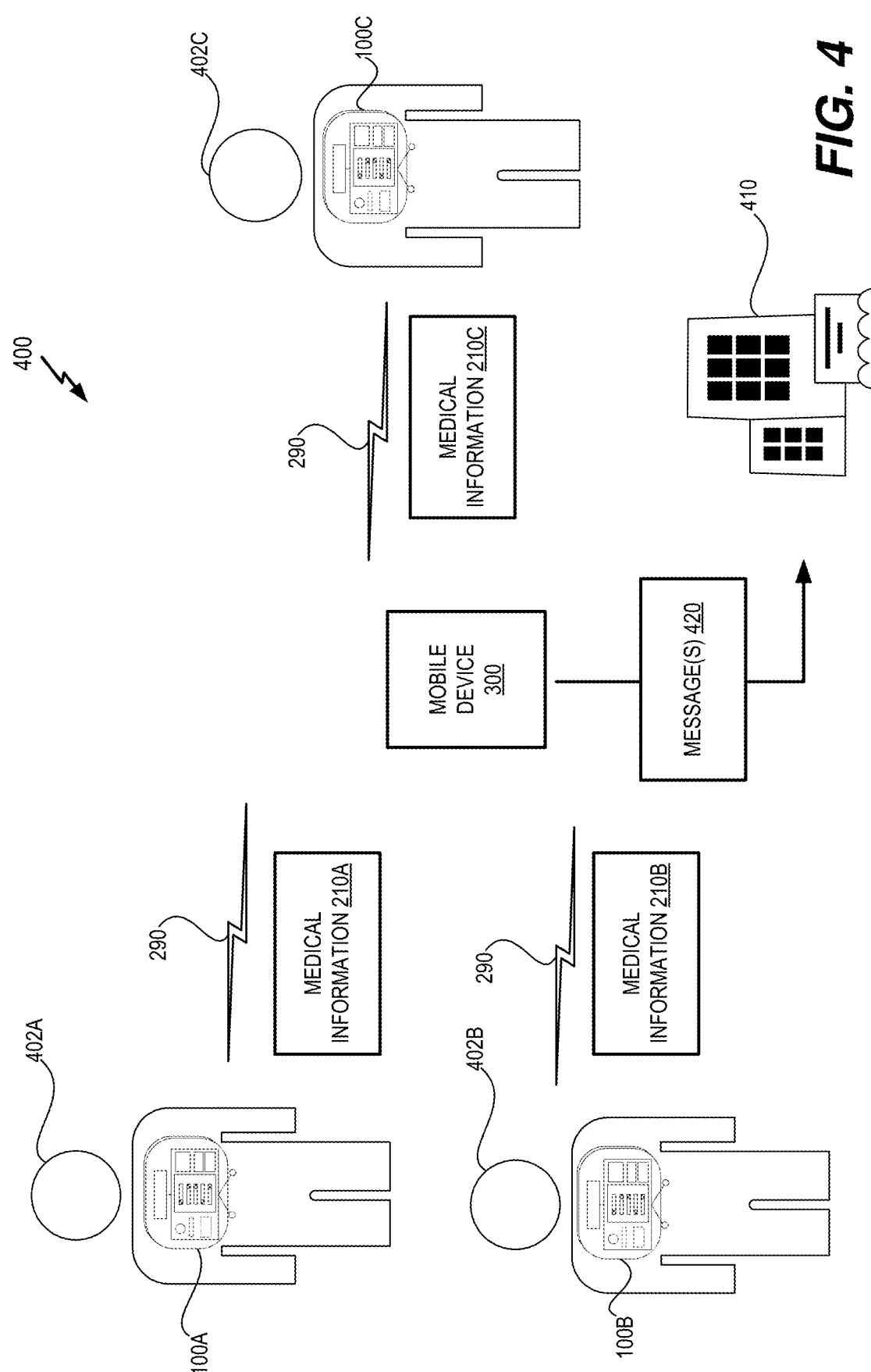
FIG. 4 is a diagram that illustrates an example of a system configured to track a patient status at a command center using a patient monitoring patch and a mobile device.

FIG. 4 depicts an example of a system 400 configured to track a patient status at a command center using patient monitoring patches and a mobile device. The system includes a plurality of patient monitoring patches 100A, 100B, 100C, the mobile device 300, and a command center 410.

In FIG. 4, a patient monitoring patch 100A is applied (e.g., attached) to a patient 402A. The patient monitoring patch 100A operates in a substantially similar manner as the patient monitoring patch 100 described with respect to FIG. 1 and has similar components. The patient monitoring patch 100A is configured to transmit, via the low-energy wireless protocol 290, medical information 210A associated with the patient 402A to the mobile device 300 in a similar manner as described with respect to FIGS. 1-2. Additionally, in FIG. 4, a patient monitoring patch 100B is applied (e.g., attached) to a patient 402B. The patient monitoring patch 100B operates in a substantially similar manner as the patient monitoring patch 100 described with respect to FIG. 1 and has similar components. The patient monitoring patch 100B is configured to transmit, via the low-energy wireless protocol 290, medical information 210B associated with the patient 402B to the mobile device 300 in a similar manner as described with respect to FIGS. 1-2. Further, in FIG. 4, a patient monitoring patch 100C is applied (e.g., attached) to a patient 402C. The patient monitoring patch 100C operates in a substantially similar manner as the patient monitoring patch 100 described with respect to FIG. 1 and has similar components. The patient monitoring patch 100C is configured to transmit, via the low-energy wireless protocol 290, medical information 210C associated with the patient 402C to the mobile device 300 in a similar manner as described with respect to FIGS. 1-2.

The mobile device 300 can be configured to generate the location information 320 as described with respect to FIG. 2. The mobile device 300 can translate the location information 320, the medical information 210A associated with the patient 402A, the medical information 210B associated with the patient 402B, and the medical information 210C associated with the patient 402C into one or more messages 420. Although the mobile device 300 is illustrated as processing medical information 210A-210C from the three patient monitoring patches 100A-100C, in other implementations, the mobile device 300 can process medical information from fewer or additional patient monitoring patches. According to one implementation, the mobile device 300 can be configured to process medical information from as many patient monitoring patches as the low-energy wireless protocol 290 can support. The mobile device 300 can transmit the one or more messages 420 to the command center 410.

The command center can locate each patient monitoring patch 100A, 100B, 100C based on the location information 320 (e.g., GPS information) associated with the mobile device 300 and can display the location of each patient monitoring patch 100A, 100B, 100C on a display map or other interface. According to one implementation, the location determination unit 310 can utilize mesh networking to determine the location of each patient monitoring patches 100A, 100B, 100C with respect to the mobile device 300. According to some implementations, the command center 410 can determine locations to dispatch each patient 402 based on user selected inputs on the patient monitoring patches 100. For example, the command center 410 can generate a command to dispatch burn victims to burn units, contagious patients to specialty holding sites, etc.

The system 400 of FIG. 4 enables the mobile device 300 to process and translate medical information 210A, 210B, 210C from a plurality of patient monitoring patches 100A, 100B, 100C. For example, the mobile device 300 can utilize a rotating query (e.g., a "round robin" query) to pair with each patient monitoring patch 100 and receive the medical information 210 from each patient monitoring patch 100. Thus, a single device 300 can pair with multiple patches 100 using the low-energy wireless protocol 290. Furthermore, by transmitting the messages 420 to the command center 410, a detailed and current status of each patient 402 can be obtained by a receiving care facility prior to arrival of the patients 402.

Referring to FIG. 5, a method of monitoring a status of multiple patients using patient monitoring patches is shown and generally designated method 500. In a particular aspect, one or more operations of the method 500 are performed by the mobile device 300.

The method 500 includes receiving, at a mobile device from a first patient monitoring patch, first medical information associated with a first patient via a low-energy wireless protocol, at block 502. For example, referring to FIG. 4, the mobile device 300 receives the medical information 210A associated with the patient 402A from patient monitoring patch 100A via the low-energy wireless protocol 290.

The method 500 includes receiving, at the mobile deice from a second patient monitoring patch, second medical information associate with a second patient via the low-energy wireless protocol, at block 504. For example, referring to FIG. 4, the mobile device 300 receives the medical information 210B associated with the patient 402B from patient monitoring patch 100B via the low-energy wireless protocol 290.

The method 500 includes generating, by the mobile device, location information indicating a location of the mobile device, at block 506. For example, referring to FIG. 3, the mobile device 300 generates the location information 320 indicating the location of the mobile device 300.

The method 500 includes translating, by the mobile device, the location information, the first medical information, and the second medical information into one or more messages, at block 508. For example, referring to FIGS. 3-4, the data translation unit 314 of the mobile device 300 translates the location information 320, the medical information 210A, and the medical information 210B into one or more messages 420.

The method 500 includes transmitting the one or more messages from the mobile device to a command center, at block 510. For example, referring to FIG. 4, the mobile device 300 transmits the one or more messages 420 to the command center 410. According to one implementation of the method 500, the one or more messages are transmitted via a FIRS TNET network. According to another implementation of the method 500, the one or more messages are transmitted via a blue force tracking network.

According to one implementation, the method 500 includes receiving, from the first patient monitoring patch, a timestamp indicating an elapsed time between an injury associated with the first patient and application of the first patient monitoring patch to the first patient. For example, the mobile device 300 can receive the timestamp 152 indicating the elapsed time between an injury associated with the patient 402A and application of the patient monitoring patch 100A to the patient 402. The method 500 can also include tracking, at the mobile device, an elapsed time since the injury based on the timestamp. For example, the elapsed time tracker 312 can track the elapsed time 322 since the injury to the patient 402A based on the timestamp 152.

The method 500 of FIG. 5 enables the mobile device 300 to process and translate medical information 210A, 210B, 210C from a plurality of patient monitoring patches 100A, 100B, 100C. Thus, a single device 300 can pair with multiple patches 100 using the low-energy wireless protocol 290 and transmit a detailed and current status of each patient 402 to a receiving care facility prior to arrival of the patients 402.

Figure 6:
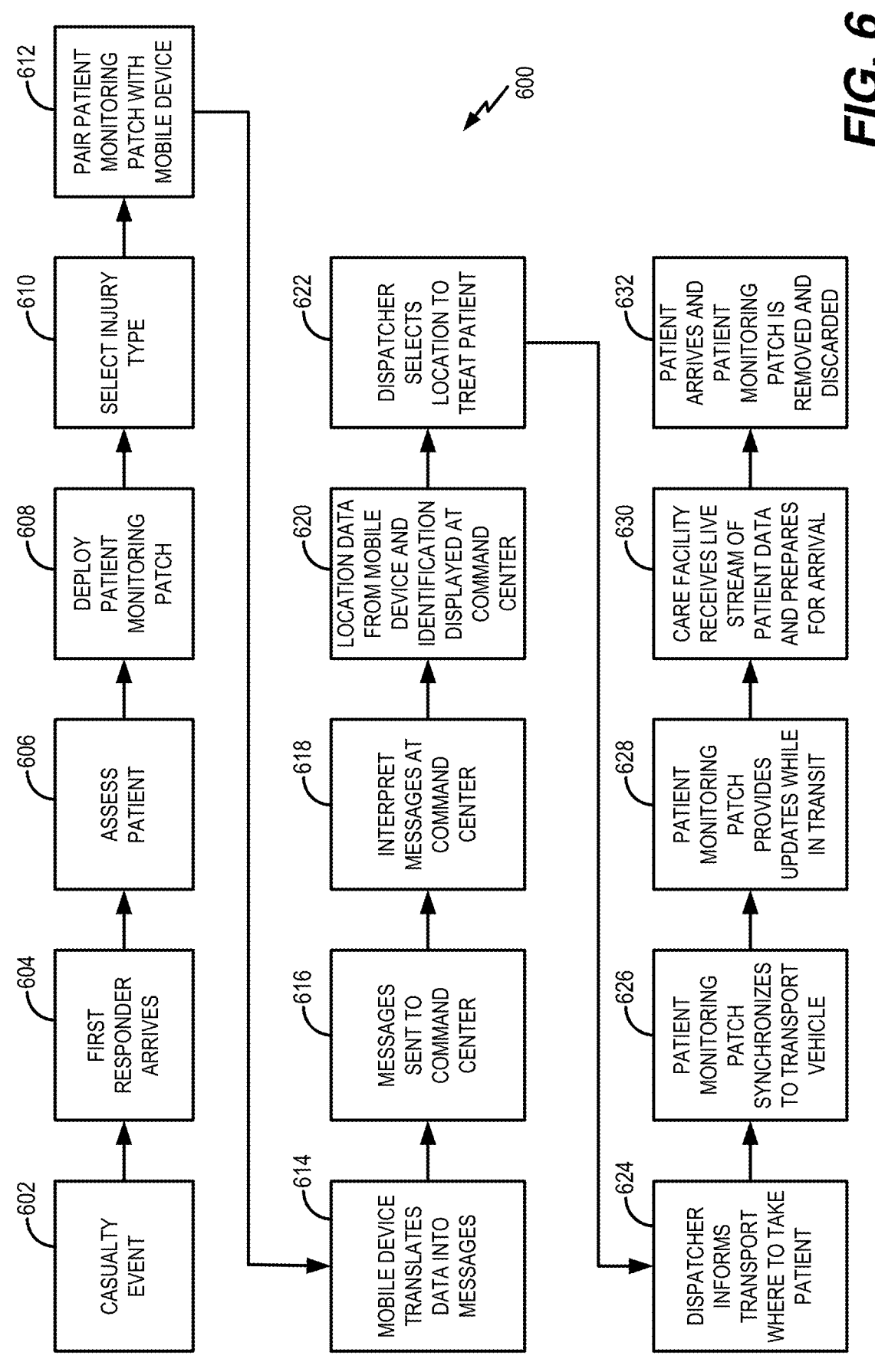
FIG. 6 is a flowchart of an example of a method of monitoring a status of a patient using a patient monitoring patch.

Referring to FIG. 6, a method of monitoring a status of a patient using a patient monitoring patch is shown and generally designated method 600. In a particular aspect, one or more operations of the method 600 are performed using the patient monitoring patch 100, the mobile device 300, the command center 410, or a combination thereof.

At block 602, a casualty event occurs. As a non-limiting example, the patient 402A could get into a car accident. It should be understood that other casualty events could occur and the car accident scenario described above is merely for illustrative purposes and should not be construed as limiting. At block 604, a first responder arrives. For example, after the car accident, one or more paramedics, police officers, or other first responders can arrive at the scene of the accident. At block 606, the first responder assesses the patient. For example, the first responder can perform an initial evaluation of the patient 402A to determine the type of injury. As a non-limiting example, the first responder can determine whether the patient 402A suffers from any blunt force trauma or whether the patient 402A is unconscious in response to the car accident.

At block 608, the first responder can deploy a patient monitoring patch. For example, the first responder can attach the patient monitoring patch 100 to the patient 402A and activate the patient monitoring patch 100 using the activation device 116. At block 610, the first responder can select the injury type on the patient monitoring patch. For example, the first responder can use the plurality of switches 108 to select the injury assessed at block 606. For illustrative purposes, the first responder can set the first switch 108A to the first state (Y) if the first responder believes the patient 402A has an altered mental state and can set the fifth switch 108E to the first state (Y) if the first responder believes the patient 402A has a blunt force trauma injury. The first responder can set the other switches 108B-108D to the second state (N) if the corresponding injuries (e.g., a puncture, a burn injury, and a gunshot injury) are not believed to be relevant. At block 612, the first responder can pair the patient monitoring patch with a mobile device. For example, the first responder can use his or her mobile device 300 to pair the mobile device 300 with the patient monitoring patch 100. According to one implementation, the first responder can use the patient monitoring patch identification number 220 to pair the patient monitoring patch 100 with the mobile device 300. According to another implementation, the mobile device 300 can automatically pair with the patient monitoring patch 100 upon activation of the patient monitoring patch 100. For example, the mobile device 300 (or an application installed on the mobile device 300) can periodically look for nearby patient monitoring patches 100 to pair. According to another implementation, the mobile device 300 can pair with the patient monitoring patch 100 by scanning a code (e.g., a QR code) on the patient monitoring patch 100.

At block 614, the mobile device can translate data into messages (e.g., text and/or data messages). For example, the data translation unit 314 can translate the medical information 210A into the messages 420 that are readily understandable by a dispatcher at the command center 410. At block 616, the mobile device can send the messages to a command center. For example, referring to FIG. 4, the mobile device 300 can send the one or more messages 420 to the command center 410. At block 618, the command center can interpret the messages. For example, referring to FIG. 4, a dispatcher at the command center 410 can interpret the messages 420 from the mobile device 300 to determine a status of the patient 402A.

At block 620, location data from the mobile device and an identification of the patient monitoring patch 100A is displayed at the command center. For example, a location associated with the location information 320 and the patient monitoring patch identification number 220 is displayed at the command center 410. Using the location information 320, the dispatcher at the command center 410 can identify the whereabouts of the patient 402A. At block 622, the dispatcher can select a location to treat the patient. For example, the dispatcher at the command center 410 can select a care facility to treat the patient 402A based on the location of the patient 402A, a capacity of the care facility, and the type of injury to the patient 402A.

At block 624, the dispatcher can inform a transport team where to take the patient. For example, after selecting the care facility to treat the patient 402A, the dispatcher at the command center 410 can use radio communications (or another form of communication) to instruct an emergency medical team where to transport the patient 402A for treatment. At block 626, the patient monitoring patch synchronizes to a transport vehicle. For example, in a similar manner that the patient monitoring patch 100A pairs with the mobile device 300 using the low-energy wireless protocol 290, the patient monitoring patch 100A can pair with a receiver in a transport vehicle (e.g., an ambulance). At block 628, the patient monitoring patch can provide updates while in transit. As a non-limiting example, the patient monitoring patch 100A can provide updated versions of the medical information 210A to the transport vehicle while the transport vehicle is in route to the care facility. As another non-limiting example, the patient monitoring patch 100A can provide updated versions of the medical information 210A to the command center 410, either directly or indirectly via the mobile device 300, and the command center 410 can route the updated medical information 210A to the care facility, hospital, etc. By routing the updated medical information 210A through the command center 410, the command center 410 can provide updated medical information 210A to different care facilities, which can be useful if the patient 402A has to go to a different care facility.

At block 630, the care facility can receive a live stream of patient data and can prepare for the arrival of the patient. For example, in a similar manner that the mobile device translates the medical information 210A, the transport vehicle can translate the medical information 210A received from the patient monitoring patch 100A and can send messages, including the translated medical information 210A, to the care facility to inform staff at the care facility of the status of the patient 402A. At block 632, the patient arrives at the care facility and the patient monitoring patch is removed and discarded.

The method 600 of FIG. 6 enables the first responder to monitor the health and status of a patient without the use of typical infrastructures that may be burdensome, such as an ambulance's support infrastructure. As a result, relatively inexperienced or untrained first responders can obtain a patient's status by applying the patient monitoring patch 100. Additionally, in scenarios in which the patient may present a danger to others, such as when the patient is believed to have an infectious disease or chemical exposure, by applying the patient monitoring patch 100 to the patient, first responders can obtain vital information about the patient while reducing extended periods of contact with the patient. It should also be appreciated that patient monitoring patch 100 may enable non-medical professionals to assist medical professionals in obtaining the patient's status. As a non-limiting example, if police arrive on the scene of an accident prior to emergency medical services, police can apply the patient monitoring patch 100 to obtain the medical status of the patient.

Additionally, the method 600 may enable periodic or occasional measurement of the patient's vital signs and periodic or occasional transmission of updated patient data to the care facility. As a result, a detailed and current status of the patient can be obtained by the care facility prior to the patient's arrival. Additionally, miscommunication of the patient data is highly unlikely, as the patient data is communicated using the wearable patch as opposed to using voice calls over radio.

Figure 7:
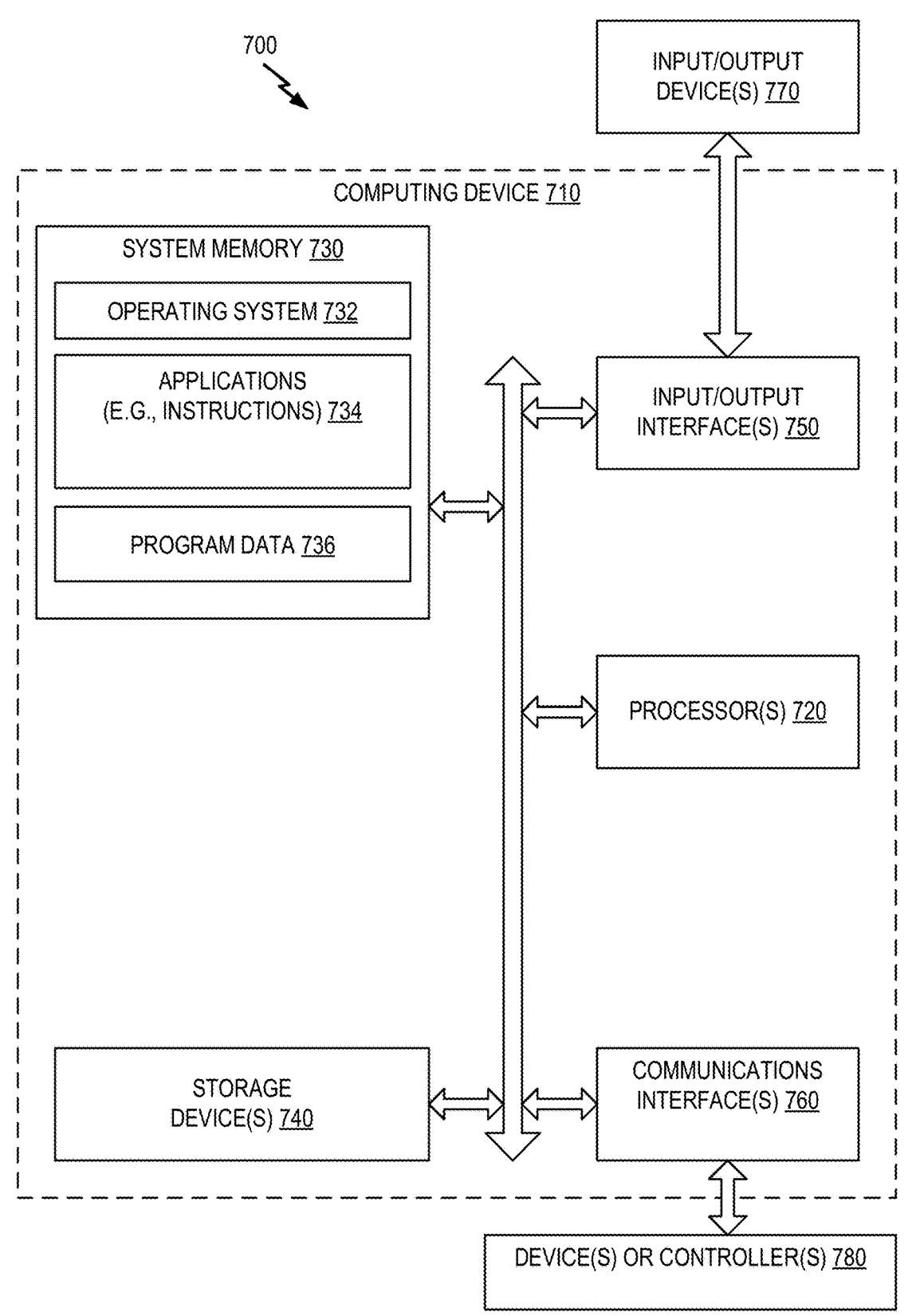
FIG. 7 is a block diagram of a computing environment including a computing device configured to support aspects of computer-implemented methods and computer-executable program instructions (or code) according to the subject disclosure.

FIG. 7 is a block diagram of a computing environment 700 including a computing device 710 configured to support aspects of computer-implemented methods and computer-executable program instructions (or code) according to the subject disclosure. For example, the computing device 710, or portions thereof, is configured to execute instructions to initiate, perform, or control one or more operations described with reference to FIGS. 1-6. According to one implementation, the computing device 710 can correspond to the circuit board 106 of the patient monitoring patch 100. According to another implementation, the computing device 710 can correspond to the mobile device 300. According to yet another implementation, the computing device 710 can correspond to one or more devices associated with the command center 410.

The computing device 710 includes one or more processors 720. The processor(s) 720 are configured to communicate with system memory 730, one or more storage devices 740, one or more input/output interfaces 750, one or more communications interfaces 760, or any combination thereof. The system memory 730 includes volatile memory devices (e.g., random access memory (RAM) devices), nonvolatile memory devices (e.g., read-only memory (ROM) devices, programmable read-only memory, and flash memory), or both. The system memory 730 stores an operating system 732, which can include a basic input/output system for booting the computing device 710 as well as a full operating system to enable the computing device 710 to interact with users, other programs, and other devices. The system memory 730 stores system (program) data 736, such as the medical information 210, the location information 320, the elapsed time 322, etc.

The system memory 730 includes one or more applications 734 (e.g., sets of instructions) executable by the processor(s) 720. As an example, the one or more applications 734 include instructions executable by the processor(s) 720 to initiate, control, or perform one or more operations described with reference to FIGS. 1-6. To illustrate, the one or more applications 734 include instructions executable by the processor(s) 720 to initiate, control, or perform one or more operations described with reference to the mobile device 300.

In a particular implementation, the system memory 730 includes a non-transitory, computer readable medium (e.g., a computer-readable storage device) storing the instructions that, when executed by the processor(s) 720, cause the processor(s) 720 to initiate, perform, or control operations to verify a vehicle position. The operations include generating location information (e.g., the location information 320)

indicating a location of a mobile device (e.g., the mobile device 300). The operations also include translating the location information, the first medical information (e.g., the medical information 210A), and the second medical information (e.g., the medical information 210B) into one or more messages (e.g., the messages 324). The operations also include transmitting the one or more messages to a command center (e.g., the command center 410).

The one or more storage devices 740 include nonvolatile storage devices, such as magnetic disks, optical disks, or flash memory devices. In a particular example, the storage devices 740 include both removable and non-removable memory devices. The storage devices 740 are configured to store an operating system, images of operating systems, applications (e.g., one or more of the applications 734), and program data (e.g., the program data 736). In a particular aspect, the system memory 730, the storage devices 740, or both, include tangible computer-readable media. In a particular aspect, one or more of the storage devices 740 are external to the computing device 710.

The one or more input/output interfaces 750 enable the computing device 710 to communicate with one or more input/output devices 770 to facilitate user interaction. For example, the one or more input/output interfaces 750 can include a display interface, an input interface, or both. For example, the input/output interface 750 is adapted to receive input from a user, to receive input from another computing device, or a combination thereof. In some implementations, the input/output interface 750 conforms to one or more standard interface protocols, including serial interfaces (e.g., universal serial bus (USB) interfaces or Institute of Electrical and Electronics Engineers (IEEE) interface standards), parallel interfaces, display adapters, audio adapters, or custom interfaces ("IEEE" is a registered trademark of The Institute of Electrical and Electronics Engineers, Inc. of Piscataway, New Jersey). In some implementations, the input/output device 770 includes one or more user interface devices and displays. The processor(s) 720 are configured to communicate with devices or controllers 780 via the one or more communications interfaces 760.

In some implementations, a non-transitory, computer readable medium stores instructions that, when executed by one or more processors 720, cause the one or more processors 720 to initiate, perform, or control operations to perform part or all of the functionality described above. For example, the instructions can be executable to implement one or more of the operations or methods of FIGS. 1-6. In some implementations, part or all of one or more of the operations or methods of FIGS. 1-6 can be implemented by one or more processors (e.g., one or more central processing units (CPUs), one or more graphics processing units (GPUs), one or more digital signal processors (DSPs)) executing instructions, by dedicated hardware circuitry, or any combination thereof.

The illustrations of the examples described herein are intended to provide a general understanding of the structure of the various implementations. The illustrations are not intended to serve as a complete description of all of the elements and features of apparatus and systems that utilize the structures or methods described herein. Many other implementations can be apparent to those of skill in the art upon reviewing the disclosure. Other implementations can be utilized and derived from the disclosure, such that structural and logical substitutions and changes can be made without departing from the scope of the disclosure. For example, method operations can be performed in a different order than shown in the figures or one or more method operations can be omitted. Accordingly, the disclosure and the figures are to be regarded as illustrative rather than restrictive.

Moreover, although specific examples have been illustrated and described herein, it should be appreciated that any subsequent arrangement designed to achieve the same or similar results can be substituted for the specific implementations shown. This disclosure is intended to cover any and all subsequent adaptations or variations of various implementations. Combinations of the above implementations, and other implementations not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features can be grouped together or described in a single implementation for the purpose of streamlining the disclosure. Examples described above illustrate but do not limit the disclosure. It should also be understood that numerous modifications and variations are possible in accordance with the principles of the subject disclosure. As the following claims reflect, the claimed subject matter can be directed to less than all of the features of any of the disclosed examples. Accordingly, the scope of the disclosure is defined by the following claims and their equivalents.

Further, the disclosure comprises embodiments according to the following examples:

Example 1 includes a device for monitoring a patient, the device comprising: a substrate; an adhesive layer coupled to a first side of the substrate, the adhesive layer configured to adhere to a patient; a circuit board coupled to a second side of the substrate; a plurality of switches coupled to the circuit board, each switch of the plurality of switches associated with a respective condition and switchable by a user between a first state indicating that a corresponding condition is believed to be associated with the patient and a second state indicating that the corresponding condition is not believed to be associated with the patient; and a wireless transmitter coupled to the circuit board, the wireless transmitter configured to transmit medical information associated with the patient to a mobile device, the medical information including data indicating a setting of each of the plurality of switches.

Example 2 includes the device of example 1, wherein the plurality of switches comprises two or more of: a first switch configured to be set to indicate whether the patient has an altered mental state; a second switch configured to be set to indicate whether the patient has a puncture; a third switch configured to be set to indicate whether the patient has a burn injury; a fourth switch configured to be set to indicate whether the patient has a gunshot injury; and a fifth switch configured to be set to indicate whether the patient has a blunt force trauma injury.

Example 3 includes the device of any of examples 1 to 2, further comprising: a first lead extending from the circuit board to a first heart-rate electrode attachable to the patient; and a second lead extending from the circuit board to a second heart-rate electrode attachable to the patient, wherein the medical information further indicates heart-rate information detected by the first heart-rate electrode and the second heart-rate electrode.

Example 4 includes the device of any of examples 1 to 3, further comprising a display device coupled to the circuit board, the display device configured to display the heart-rate information.

Example 5 includes the device of any of examples 1 to 4, further comprising: a battery coupled to the circuit board; and an activation device configured to activate the circuit board via battery power associated with the battery.

Example 6 includes the device of any of examples 1 to 5, further comprising a voltage-boost integrated circuit coupled to the battery and to the circuit board, the voltage-boost integrated circuit configured to provide a regulated voltage to the circuit board.

Example 7 includes the device of any of examples 1 to 6, wherein the wireless transmitter comprises a low-energy wireless transmitter.

Example 8 includes the device of any of examples 1 to 7, further comprising a temperature sensor coupled to the circuit board, the temperature sensor configured to detect a temperature of the patient, wherein the medical information further indicates the temperature of the patient.

Example 9 includes the device of any of examples 1 to 8, further comprising a user interface coupled to the circuit board and configured to receive a user input indicating a timestamp.

Example 10 includes a system comprising: a first patient monitoring patch configured to transmit first medical information associated with a first patient to a mobile device via a low-energy wireless protocol; a second patient monitoring patch configured to transmit second medical information associated with a second patient to the mobile device via the low-energy wireless protocol; and the mobile device configured to: generate location information indicating a location of the mobile device; translate the location information, the first medical information, and the second medical information into one or more messages; and transmit the one or more messages to a command center.

Example 11 includes the system of example 10, wherein the first patient monitoring patch is further configured to: periodically update the first medical information; and transmit an updated version of the first medical information to the mobile device.

Example 12 includes the system of any of examples 10 to 11, wherein the one or more messages are transmitted using a cellular communication protocol.

Example 13 includes the system of any of examples 10 to 12, wherein the first patient monitoring patch comprises a plurality of switches, each switch of the plurality of switches associated with a respective condition and switchable by a user between a first state indicating that a corresponding condition is believed to be associated with the first patient and a second state indicating that the corresponding condition is not believed to be associated with the first patient.

Example 14 includes the system of any of examples 10 to 13, wherein each switch of the plurality of switches corresponds to a physical switch.

Example 15 includes the system of any of examples 10 to 14, wherein the mobile device is further configured to encrypt the one or more messages prior to transmission of the one or more messages to the command center.

Example 16 includes a method comprising: receiving, at a mobile device from a first patient monitoring patch, first medical information associated with a first patient via a low-energy wireless protocol; receiving, at the mobile device from a second patient monitoring patch, second medical information associated with a second patient via the low-energy wireless protocol; generating, by the mobile device, location information indicating a location of the mobile device; translating, by the mobile device, the location information, the first medical information, and the second medical information into one or more messages; and transmitting the one or more messages from the mobile device to a command center.

Example 17 includes the method of example 16, wherein the one or more messages are transmitted via a FIRSTNET network.

Example 18 includes the method of example 16, wherein the one or more messages are transmitted via a blue force tracking network.

Example 19 includes the method of any of examples 16 to 18, wherein the first patient monitoring patch comprises a plurality of switches, each switch of the plurality of switches associated with a respective condition and switchable by a user between a first state indicating that a corresponding condition is believed to be associated with the first patient and a second state indicating that the corresponding condition is not believed to be associated with the first patient.

Example 20 includes the method of any of examples 16 to 19, further comprising: receiving, from the first patient monitoring patch, a timestamp indicating an elapsed time between an injury associated with the first patient and application of the first patient monitoring patch to the first patient; and tracking, at the mobile device, an elapsed time since the injury based on the timestamp.

What is claimed is:

1. A system comprising:

a first patient monitoring patch configured to transmit first medical information associated with a first patient to a first mobile device via a low-energy wireless protocol, wherein the first patient monitoring patch includes a first plurality of input interfaces configured to identify a first particular injury location, and wherein the first patient monitoring patch includes a third plurality of input interfaces configured to identify a first patient injury type, the first plurality of input interfaces distinct from the third plurality of input interfaces;

a second patient monitoring patch configured to transmit second medical information associated with a second patient to the first mobile device via the low-energy wireless protocol, wherein the second patient monitoring patch includes a second plurality of input interfaces configured to identify a second particular injury location, and wherein the second patient monitoring patch includes a fourth plurality of input interfaces configured to identify a second patient injury type, the second plurality of input interfaces distinct from the fourth plurality of input interfaces;

the first mobile device configured to:

generate location information indicating a location of the first mobile device;

translate the location information, the first medical information, and the second medical information into one or more first messages; and transmit the one or more first messages to a command center; and a second mobile device coupled to a transport vehicle, the second mobile device configured to:

synchronize with the first patient monitoring patch and the second patient monitoring patch;

receive third medical information associated with the first patient from the first patient monitoring patch via the low-energy wireless protocol after the second mobile device synchronizes with the first patient monitoring patch while the transport vehicle is in motion;

receive fourth medical information associated with the second patient from the second patient monitoring patch via the low-energy wireless protocol after the second mobile device synchronizes with the second patient monitoring patch while the transport vehicle is in motion;

translate the third medical information and the second medical information into one or more second messages; and transmit the one or more second messages to a destination of the transport vehicle.

2. The system of claim 1, wherein the first patient monitoring patch is further configured to:

periodically update the first medical information; and transmit an updated version of the first medical information to the first mobile device.

3. The system of claim 1, wherein the first patient monitoring patch is further configured to couple to the first patient and acquire the first medical information via a first sensor in contact with the first patient while the first patient monitoring patch is coupled to the first patient, and wherein the second patient monitoring patch is further configured to couple to the second patient and acquire the second medical information via a second sensor in contact with the second patient while the second patient monitoring patch is coupled to the second patient.

4. The system of claim 1, wherein the first patient monitoring patch comprises a plurality of switches, each switch of the plurality of switches associated with a respective condition and switchable by a user between a first state indicating that a corresponding condition is believed to be associated with the first patient and a second state indicating that the corresponding condition is not believed to be associated with the first patient.

5. The system of claim 1, wherein the one or more second messages include a vehicle position.

6. The system of claim 1, wherein the first patient monitoring patch comprises:

a substrate;

an adhesive layer coupled to a first side of the substrate, the adhesive layer configured to adhere to the first patient;

a circuit board coupled to a second side of the substrate;

a plurality of switches coupled to the circuit board, each switch of the plurality of switches associated with a respective condition and switchable by a user between a first state indicating that a corresponding condition is believed to be associated with the first patient and a second state indicating that the corresponding condition is not believed to be associated with the first patient, the third plurality of input interfaces including the plurality of switches; and a wireless transmitter coupled to the circuit board, the wireless transmitter configured to transmit the first medical information associated with the first patient to the first mobile device, the first medical information including data indicating a setting of each of the plurality of switches.

7. The system of claim 6, wherein the plurality of switches comprises two or more of:

a first switch configured to be set to indicate whether the first patient has an altered mental state;

a second switch configured to be set to indicate whether the first patient has a puncture;

a third switch configured to be set to indicate whether the first patient has a burn injury;

a fourth switch configured to be set to indicate whether the first patient has a gunshot injury; and a fifth switch configured to be set to indicate whether the first patient has a blunt force trauma injury.

8. The system of claim 6, further comprising:

a first lead extending from the circuit board to a first heart-rate electrode attachable to the first patient; and a second lead extending from the circuit board to a second heart-rate electrode attachable to the first patient, wherein the first medical information further indicates heart-rate information detected by the first heart-rate electrode and the second heart-rate electrode.

9. The system of claim 8, further comprising a display device coupled to the circuit board, the display device configured to display the heart-rate information.

10. The system of claim 6, further comprising:

a battery coupled to the circuit board; and an activation device configured to activate the circuit board via battery power associated with the battery.

11. The system of claim 10, further comprising a voltage-boost integrated circuit coupled to the battery and to the circuit board, the voltage-boost integrated circuit configured to provide a regulated voltage to the circuit board.

12. The system of claim 6, wherein the wireless transmitter comprises a low-energy wireless transmitter.

13. The system of claim 6, further comprising a temperature sensor coupled to the circuit board, the temperature sensor configured to detect a temperature of the first patient, wherein the first medical information further indicates the temperature of the first patient.

14. The system of claim 6, further comprising a user interface coupled to the circuit board and configured to receive a user input indicating a timestamp.

15. A system comprising:

a first patient monitoring patch configured to transmit first medical information associated with a first patient to a first mobile device via a low-energy wireless protocol, wherein the first patient monitoring patch includes a first plurality of input interfaces configured to identify a first particular injury location, and wherein the first plurality of input interfaces includes a light emitting diode button associated with a particular location on a body of the first patient;

a second patient monitoring patch configured to transmit second medical information associated with a second patient to the first mobile device via the low-energy wireless protocol, wherein the second patient monitoring patch includes a second plurality of input interfaces configured to identify a second particular injury location;

the first mobile device configured to:

generate location information indicating a location of the first mobile device;

translate the location information, the first medical information, and the second medical information into one or more first messages; and transmit the one or more first messages to a command center; and a second mobile device coupled to a transport vehicle, the second mobile device configured to:

synchronize with the first patient monitoring patch and the second patient monitoring patch;

receive third medical information associated with the first patient from the first patient monitoring patch via the low-energy wireless protocol after the second mobile device synchronizes with the first patient monitoring patch while the transport vehicle is in motion;

receive fourth medical information associated with the second patient from the second patient monitoring patch via the low-energy wireless protocol after the second mobile device synchronizes with the second patient monitoring patch while the transport vehicle is in motion;

translate the third medical information and the second medical information into one or more second messages; and transmit the one or more second messages to a destination of the transport vehicle.

16. A method comprising:

receiving, at a first mobile device from a first patient monitoring patch, first medical information associated with a first patient via a low-energy wireless protocol, wherein the first patient monitoring patch includes a first plurality of input interfaces configured to identify a first particular injury location, wherein the first patient monitoring patch includes a third plurality of input interfaces configured to identify a first patient injury type, the first plurality of input interfaces distinct from the third plurality of input interfaces, and wherein the first medical information includes a first input from at least one of the first plurality of input interfaces and a third input from at least one of the third plurality of input interfaces;

receiving, at the first mobile device from a second patient monitoring patch, second medical information associated with a second patient via the low-energy wireless protocol, wherein the second patient monitoring patch includes a second plurality of input interfaces configured to identify a second particular injury location, and wherein the second patient monitoring patch includes a fourth plurality of input interfaces configured to identify a second patient injury type, the second plurality of input interfaces distinct from the fourth plurality of input interfaces, and wherein the second medical information includes a second input from at least one of the second plurality of input interfaces and a fourth input from at least one of the fourth plurality of input interfaces;

generating, by the first mobile device, location information indicating a location of the first mobile device;

translating, by the first mobile device, the location information, the first medical information, and the second medical information into one or more first messages;

transmitting the one or more first messages from the first mobile device to a command center;

synchronizing a second mobile device coupled to a transport vehicle with the first patient monitoring patch and the second patient monitoring patch;

receiving, at the second mobile device, third medical information associated with the first patient from the first patient monitoring patch via the low-energy wireless protocol after the second mobile device synchronizes with the first patient monitoring patch while the transport vehicle is in motion;

receiving, at the second mobile device, fourth medical information associated with the second patient from the second patient monitoring patch via the low-energy wireless protocol after the second mobile device synchronizes with the second patient monitoring patch while the transport vehicle is in motion;

translating, at the second mobile device, the third medical information and the second medical information into one or more second messages; and transmitting, at the second mobile device, the one or more second messages to a destination of the transport vehicle.

17. The method of claim 16, wherein the one or more first messages are transmitted via a FIRSTNET network.

18. The method of claim 16, wherein the one or more first messages are transmitted via a blue force tracking network.

19. The method of claim 16, wherein the first patient monitoring patch comprises a plurality of switches, each switch of the plurality of switches associated with a respective condition and switchable by a user between a first state indicating that a corresponding condition is believed to be associated with the first patient and a second state indicating that the corresponding condition is not believed to be associated with the first patient.

20. The method of claim 16, further comprising:

receiving, from the first patient monitoring patch, a timestamp indicating an elapsed time between an injury associated with the first patient and application of the first patient monitoring patch to the first patient; and tracking, at the first mobile device, an elapsed time since the injury based on the timestamp.

* * * * *